(12) United States Patent
Day et al.

(10) Patent No.: US 6,602,296 B1
(45) Date of Patent: Aug. 5, 2003

(54) CHEMICAL SUPPLEMENTATION OF BONE

(75) Inventors: Robert Edward Day, East Fremantle (AU); Stephen Manfred Megson, Darlington (AU); David John Wood, Floreat (AU)

(73) Assignee: The University of Western Australia, Nedland (AU)

( * ) Notice: Subject to any disclaimer, the term of this patent is extended or adjusted under 35 U.S.C. 154(b) by 0 days.

(21) Appl. No.: 09/508,318

(22) PCT Filed: Sep. 9, 1998

(86) PCT No.: PCT/AU98/00736

§ 371 (c)(1),
(2), (4) Date: Jun. 15, 2000

(87) PCT Pub. No.: WO99/12554

PCT Pub. Date: Mar. 18, 1999

(30) Foreign Application Priority Data

Sep. 9, 1997 (AU) .............................. PO 9076

(51) Int. Cl.[7] .............................. A61F 11/00
(52) U.S. Cl. .................. 623/919; 623/23.49; 623/16.11
(58) Field of Search ........................... 623/23.49, 23.61, 623/23.62, 23.63, 23.72, 919, 925, 16.11; 128/898; 424/422–424; 523/113–115; 604/500–502, 505

(56) References Cited

U.S. PATENT DOCUMENTS

| 4,610,692 A | * | 9/1986 | Eitenmuller et al. ........... 623/16 |
| 4,853,225 A | * | 8/1989 | Wahlig et al. ............... 424/423 |
| 5,023,085 A | * | 6/1991 | Francoeur et al. ........... 424/449 |
| 5,077,049 A | | 12/1991 | Dunn et al. |
| 5,258,420 A | * | 11/1993 | Posey-Dowty et al. ..... 523/116 |
| 5,278,201 A | | 1/1994 | Dunn et al. |
| 5,278,202 A | | 1/1994 | Dunn et al. |
| 5,324,519 A | | 6/1994 | Dunn et al. |
| 5,340,849 A | | 8/1994 | Dunn et al. |
| 5,368,859 A | | 11/1994 | Dunn et al. |
| 5,487,897 A | | 1/1996 | Polson et al. |
| 5,599,552 A | | 2/1997 | Dunn et al. |
| 5,632,727 A | | 5/1997 | Tipton et al. |
| 5,668,120 A | * | 9/1997 | Shinoda et al. ............. 514/102 |
| 5,681,873 A | | 10/1997 | Norton et al. |
| 5,702,716 A | | 12/1997 | Dunn et al. |
| 5,707,647 A | | 1/1998 | Dunn et al. |
| 5,717,030 A | | 2/1998 | Dunn et al. |
| 5,725,491 A | | 3/1998 | Tipton et al. |
| 5,733,950 A | | 3/1998 | Dunn et al. |
| 5,736,152 A | | 4/1998 | Dunn et al. |
| 5,739,176 A | | 4/1998 | Dunn et al. |
| 5,744,153 A | | 4/1998 | Yewey et al. |
| 5,759,563 A | | 6/1998 | Yewey et al. |
| 5,780,044 A | | 7/1998 | Yewey et al. |
| 5,792,469 A | | 8/1998 | Tipton et al. |
| 5,873,849 A | * | 2/1999 | Bernard ....................... 604/20 |
| 5,888,533 A | | 3/1999 | Dunn et al. |
| 5,935,598 A | * | 8/1999 | Sage et al. .................. 424/449 |
| 5,941,909 A | * | 8/1999 | Purkait ....................... 623/11 |
| 5,945,115 A | | 8/1999 | Dunn et al. |
| 5,990,194 A | | 11/1999 | Dunn et al. |
| 6,008,206 A | * | 12/1999 | Dohi et al. .................. 514/108 |
| 6,071,530 A | | 6/2000 | Polson et al. |
| 6,120,789 A | | 9/2000 | Dunn |
| 6,143,314 A | | 11/2000 | Chandrashekar et al. |
| 6,261,583 B1 | | 7/2001 | Dunn et al. |

* cited by examiner

Primary Examiner—David J. Isabella
Assistant Examiner—Urmi Chattopadhyay
(74) Attorney, Agent, or Firm—Frommer Lawrence & Haug LLP; Thomas J. Kowalski, Esq.

(57) ABSTRACT

Disclosed and claimed is bone or bone tissue supplemented with a therapeutically effective compound and methods for supplementing bone or bone tissue with the therapeutically effective compound.

18 Claims, 12 Drawing Sheets

CHEMICAL SUPPLEMENTATION OF BONE

The present invention provides bone and bone tissue supplemented with at least a therapeutically useful compound and in particular relates to a method for supplementing bone and or bone tissue with said compound(s).

Major allograft surgery has provided a solution to many reconstructive problems in musculoskeletal and maxillofacial surgery. The use of such surgery remains however, retarded by the frequency of infections that are often a disabling complication of such surgery. While the use of small frozen allografts has a very low rate of infection, major allografts have infection rates between 5 and 13%. This susceptibility to infection is probably multifactorial, with avascularity and antigenicity of the implanted graft contributing as well as the frequent extensive soft tissue excision, and potential for wound breakdown.

The use of allograft bone in orthopaedic practice is now well established both as morsellised and site specific structural grafts. The risk of infection, however remains a major complicating factor with such surgery. Like other forms of allograft surgery, the frequency of infection with allograft bone varies between 5 and 13.3%. The outcome in patients who develop infection is poor and often requires either two stage revision or amputation.

Infections typically arise early after allograft surgery with 75% of cases presenting within 4 months. Perioperative introduction of organisms is the presumptive mode of infection in the majority of these cases. The most common organisms isolated are gram positive (54%) followed by gram negative (36%) and mixed (10%).

Numerous attempts have been made to lessen the rate of infection in allograft surgery, particularly in the field of maxillofacial surgery. Perioperative antibiotic regimes are often employed, involving prolonged administration of antibiotics for up to 3 months, although no controlled studies have been performed to show the efficacy of these regimes. The theoretical problem of systemic antibiotic administration in allograft surgery, particularly when using allograft bone is that the allografts are initially avascular and the antibiotics do not reach their target.

Attempts have been made to load allograft bone with antibiotics. In one such study morsellised graft was mixed with antibiotic solutions. More recently antibiotic supplemented bone allograft has been developed and used in the area of avulsive defects of the oral and maxillofacial skeleton. This technique employs demineralised particulate allograft bone and mixes it with purified gelatine powder and cephalothin and tobramycin. A canine model to test this preparation has shown a probable protection from post-operative infection when compared with conventional allografts.

Although these methods have been shown to display a decreased complication rate, the problem of infection in major allograft bone surgery is still a major concern. Furthermore, present methods of preparing allograft bone against infection require a large amount of preparatory work, are typically unsuitable where large bone grafts are required and depending on the methods used may not result in a product that has the same structural integrity as allograft bone. Thus, the problem of infection in major allograft bone surgery is largely unsolved and has severe consequences to patients who develop complications.

The present invention seeks to provide an improved bone and or bone tissue supplemented with at least a therapeutically useful compound. Moreover, the invention seeks to provide a simple and effective procedure for supplementing bone and or bone tissue with at least a therapeutically effective compound.

Throughout the specification, unless the context requires otherwise, the word "comprise" or variations such as "comprises" or "comprising", will be understood to imply the inclusion of a stated integer or group of integers but not the exclusion of any other integer or group of integers.

For the purposes of the present invention the phrase "bone and bone tissue" encompasses bone substitutes which comprise any biological or synthetic material used to substitute for bone during reconstruction including material processed from xenograft sources and chemicals manufactured for bone substitute purposes such as calcium phosphate and hydroxyappatite.

The present invention consists in a bone or bone tissue supplemented with at least a therapeutically useful compound, wherein said compound is concentrated within the bone matrix.

Unlike prior art products the present invention does not rely upon the use of binders, protective agents, gelatinisation agents or the like to associate therapeutic compounds with allograft bone or tissue. Rather, therapeutically effective compounds are delivered to and concentrated with the bone matrix by a process of iontophoresis. Preferably the concentration of the therapeutically effective compound within the bone is greater than the amount of therapeutically effective compound that might be absorbed into bone as a result of simple diffusion. It will be appreciated that the relative amount of therapeutic compound which might be loaded into any particular piece of bone will depend on (a) the safe in situ usage limits for that therapeutic compound, (b) the characteristics of the bone or bone tissue, (c) the biochemical characteristics of the particular compound selected and (d) the particular purpose for which the bone or bone tissue is being used.

Therapeutically effective compounds that might be employed in the invention include, but are not limited to: antibiotics, antifungal compounds and chemotherapeutic compounds, tissue growth factors (for example bone morphogenic protein), non-steroidal anti-inflammatory agents, such as indomethacin, neuromuscular agents affecting calcium and bone metabolism (such as calcitonin), anti-viral agents, anti-tuberculosis agents (such as rifampicin), anthelmintic agents (such as mebendazole), antiseptic agents, vitamins and minerals. Most preferably, the compounds that are loaded into the bone are compounds that form a salt in solution and ionise to a single positive or negative ion. Those of ordinary skill in the art will know such compounds.

If, for example, antibiotics are to be loaded into the bone or bone tissue the antibiotic compound is preferably selected from the following: flucloxacillin, gentamicin, cephalothin, ticarcillin, ciprofloxacin, nenzl-peniccillin, cefoperazone, cefuroxime, cephazolin and tobramycin. Most preferably the antibiotic is either flucloxacillin or gentamicin. When loaded into bone these compounds are preferably present at a concentration of between the minimum inhibitory concentration of the antibiotic and the concentration that would provide a total amount of antibiotic equal to the safe maximum single dose for systemic administration. For example, the maximum dose of gentamicin that might be loaded into allograft bone is about 200 mg/kg while the maximum dose of flucloxacillin is about 80 mg/kg.

If the therapeutically effective compound is an antifungal compound, the antifungal compound is preferably selected from the following: miconazole, and ketaconazole. When loaded into bone, these compounds are preferably present at a concentration of between the minimum inhibitory concentration of the antifungal and the concentration that would provide a total amount of antifungal equal to the safe maximum single dose for systemic administration.

If the therapeutically effective compound is a chemotherapeutic compound the chemotherapeutic is preferably selected from the following: 5-fluoro-uracil and vinblastin. Most preferably the chemotherapeutic is 5-fluoro-uracil.

In an alternative form, the present invention consists of a method for supplementing bone or bone tissue with a therapeutically effective compound, wherein said method employs the steps of:

(i) Exposing bone or bone tissue to a therapeutically effective compound; and (ii) Applying a potential difference across said bone or bone tissue such that the therapeutically effective compound is concentrated within the bone or bone tissue.

Preferably, the therapeutically effective compound employed in the method is concentrated within the bone or bone tissue using an externally applied potential difference. Any externally applied potential difference may be used in the method, provided that it does not destroy the structural integrity of the bone or bone tissue. The potential difference that is used will depend on: (a) the thickness of the bone, (b) the time available to deliver the compound to the bone, (c) the compound which is to be loaded into the bone and (d) the temperature of the bone. Preferably the temperature of the bone during the loading process should be maintained below about 37° C.

If highly externally applied potential differences are being used to load the bone with a therapeutically effective compound, then the method should be carried out in the presence of a means which is capable of cooling the bone or bone tissue. For example the method might be carried out in a refrigerated environment or alternatively might be carried out in a water bath.

It will be appreciated that the present invention is not limited to the loading of sectioned allograft bone. It might also be used in situ to deliver compounds into bone to treat medical disorders such as bone tumours. In such circumstances the therapeutically effective compound is preferable introduced at medically safe levels into the tissue surrounding the bone. An externally applied potential difference is then applied across the bone for sufficient time to concentrate the therapeutically effective compound within the bone. Preferably, the externally applied potential difference is selected such that it is capable of drawing and concentrating the therapeutically effective compound into the bone but does not effect the structural integrity of the surrounding tissue.

Therapeutically effective compounds suitable for use in the method are those which are capable of forming a soluble salt in solution. Preferably the compounds selected are capable of ionising in the presence of an externally applied potential difference to form either positive or negative ions. Examples of suitable compounds are described above. Most preferably antibiotics such as flucloxacillin and gentamicin are used as the therapeutically effective compounds.

The concentration of therapeutically effective compounds that may be loaded into the bone or bone tissue will depend largely on the properties of the compound used and the time over which the compound is required to have a therapeutic effect. Preferably the compound is concentrated within the bone to a level which exceeds the amount of compound that might be diffused into the bone as a result of diffusion over an equivalent period of time. That is, when both the present method and a diffusion method are carried out over an equivalent period of time.

Applying an external potential difference across bone or bone tissue requires the use of at least two electrodes, one being located on one side of the bone and the other being suitably positioned on the other side of the bone. To ensure electrical contact between the electrodes they are each preferably surrounded by a medium capable of conducting electrical current. Preferably there is a plurality of electrodes on either side of the bone. While any electrode might be used in the method, the preferred electrodes are those that do not produce a chemical residue that would damage the bone or bone tissue. Suitable electrodes for use in the invention include, but are not limited to, carbon, platinum, titanium, gold, noble metals, stainless steel, conductive plastic and the like.

In a highly preferred form of the invention the method is applied to allograft bone to load the bone with suitable therapeutic compounds prior to or during allograft surgery. Preferably the method is performed under aseptic conditions.

According to a particularly preferred form of the method, the section of bone to be treated is prepared and defrosted. It is then cut (in a manner which would be well known to those in skilled in the art) to an appropriate length with a slight excess at each end. Preferable that excess is in the order of about 1 to 10 mm.

To one end of the bone, a disc of an appropriate size to completely seal the medullary canal at that end is sealingly engaged to the bone. The disc can be made of any insulating material, such as acrylic, plastic etc. Sealing engagement between the bone and the disc may be achieved using, for example, a glue which is capable of bonding the disc to the bone, such as cyanoacrylate, and which is capable of being sterilised. Those of ordinary skill in the art will know such glues.

Figure 1:
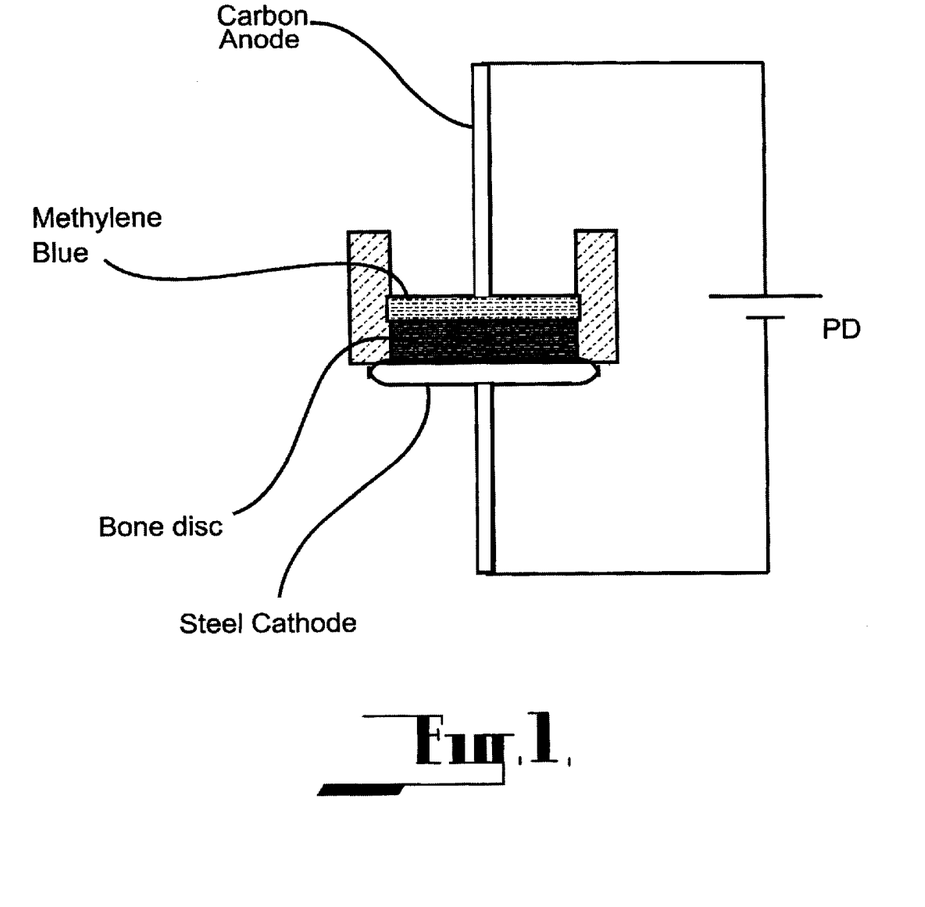
FIG. 1 illustrates a representative apparatus for transverse iontophoresis.

To the opposite end of the bone, a tube of an appropriate length is cemented to the bone, such that the tube sealingly engages onto the end the medullary canal (see FIG. 1). The tube can be made of any insulating material, such as acrylic. The specimen is then placed in a beaker and immersed in a buffer solution such that the open end of the extended medullary canal is just above the level of the ionic solution. The buffer solution can be any solution capable of conducting electrical current, such as normal saline.

The medullary canal is then filled with an ionic solution of the compound to be loaded into the bone. Desirably the solution is sterile and consists of an antibiotic in ionic form such as gentamicin or flucloxacillin, but may also consist of antifungal compounds, chemotherapeutic agents or any other compound that ionises to a single ionic species in solution. The pH of solution should then be optimised to ensure maximal ionisation of compound.

Electrodes are then placed in the apparatus, with at least one placed vertically in the ionic solution, and a plurality of vertical, equally spaced electrodes fixed to the side of the beaker, immersed in the buffer solution. The surrounding electrodes should then be connected electrically such that they act as one electrode. The electrodes can be made of any inert material such as carbon, or platinum.

A potential difference is then applied across the electrodes until loading of the therapeutically effective compound into the bone is complete. The time required for the compound to be transferred in to the bone tissue will depend on (a) the voltage—with increasing voltage the shorter the time period is required for transfer of the compound, (b) the thickness of the bone (c) the ionic compound used. Typically the maximum voltage that might be used in the method without the assistance of a suitable cooling means would be in the order of 100 V, although there is theoretically no upper or lower limit to the voltage that can be used when a cooling means is employed. Desirably the temperature of the bone should not reach or exceed 37° C., at which temperature the collagen component of bone begins to degrade.

Voltages and times for application may be determined experimentally as described in the following examples.

BRIEF DESCRIPTION OF DRAWINGS

The present invention is further described by the following non-limiting Figures and Examples.

Further features of the present invention are more fully described in the following Examples. It is to be understood, however, that this detailed description is included solely for the purposes of exemplifying the invention, and should not be understood in any way as a restriction on the broad description as set out above.

EXAMPLES

Example 1

Experimental work was carried out using mature Merino Sheep tibiae accessed from 'butcher's shops', and later using Human allograft bone which was rejected for implantation by the Perth Bone and Tissue Bank. The ionic compound used initially was methylene blue in 1% solution which forms positive ions and migrates away from the anode when a potential difference is applied, flucloxacillin and gentamicin were the antibiotics selected as the antibiotics for further study. Methylene blue was chosen for the initial work because its ease of visual identification obviated the need for assay techniques. It has a molecular weight of 373 which is not very different from that of flucloxacillin (453) and gentamicin (460). This similarity means that it provides a good model to study the likely behaviour patterns of flucloxacillin and gentamicin ions using iontophoresis. Gentamicin exists in solution as positive ions of the sulphate salt, and flucloxacillin as negative ions and ionic aggregates of its sodium salt.

Preliminary work was done using 1 $cm^2$ discs or squares of cortical bone and was used to establish whether iontophoresis was effective in facilitating the movement of methylene blue ions in bone. In addition the technical aspects of how the technique's efficacy could be maximised were studied with particular reference to: The direction in which methylene blue is moved easiest under the influence of a potential difference through cortical bone; The effect of a pulsed field as compared with a unipolar potential gradient on the movement of ions; and the effects of varying the potential difference on the rate of movement of ions across the bone.

Figure 2:
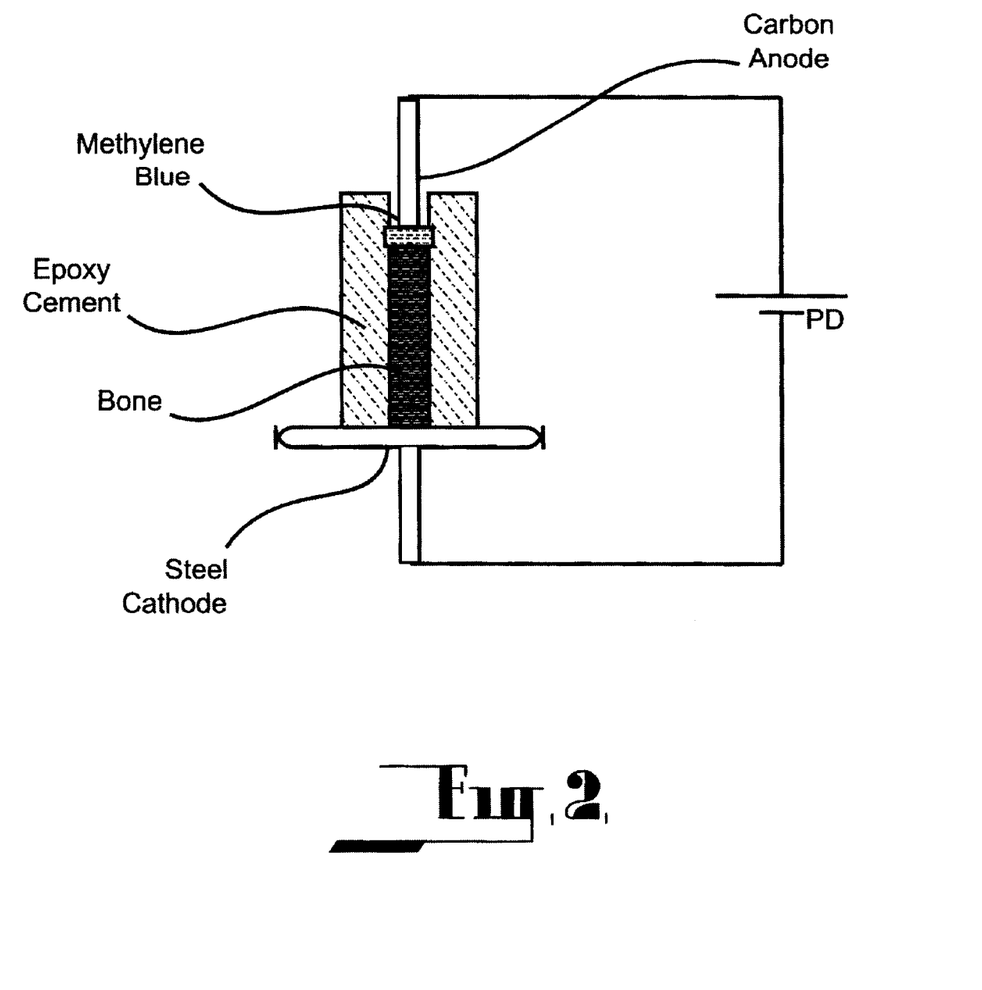
FIG. 2 illustrates a representative apparatus for longitudinal or circumferential iontophoresis.
Figure 3:
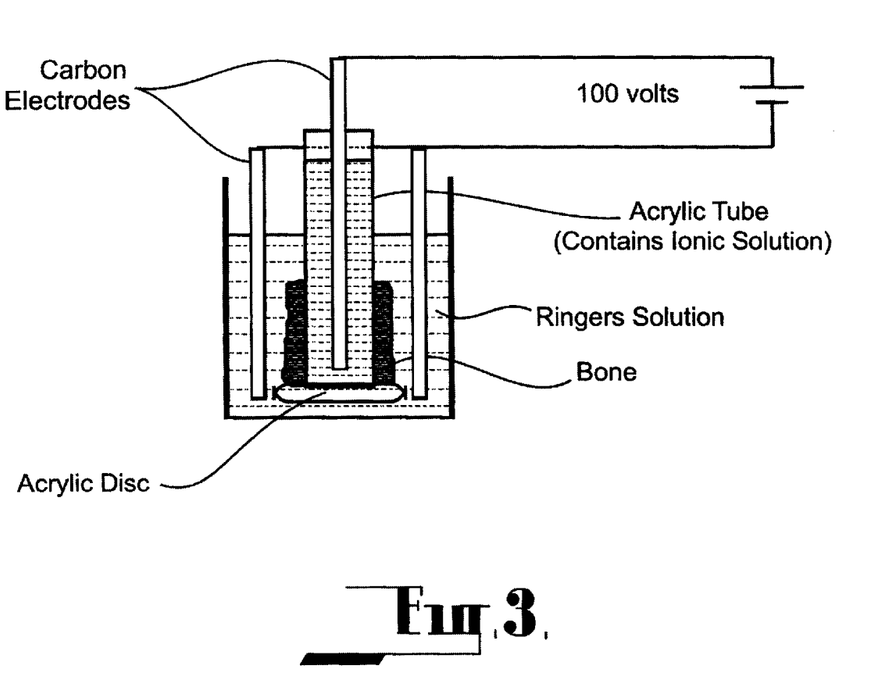
FIG. 3 illustrates a apparatus for iontophoresis of tubular bone specimens.

Pieces of bone were imbedded in epoxy cement, as an electrical insulator, leaving 2 surfaces free to apply the iontophoretic gradient across. The specimens were then sectioned and the penetration of the methylene blue measured. The apparatus used is shown in FIGS. 1 & 2.

These served to study the feasibility of iontophoresis in bone, and the most effective method of applying the technique. Control experiments where methylene blue was applied to one surface of the cortical bone disc revealed very minimal penetration of the blue colour even after 20 minutes. In cases where a potential difference was applied the methylene blue was observed to migrate through the cortices.

The rate of facilitated diffusion was proportional to the potential difference applied and at 100 volts across a 4 mm cortex, full penetration could be expected at approximately 4 minutes. There was no advantage apparent from using a pulsed field, as polarisation of the electrodes with a consequent fall in the current being passed appears to occur at about the time of full cortical penetration, by the ions under investigation, and is therefore of little consequence. The technique was most effective in moving ions transversely across the cortex. It was less effective at moving ions circumferentially around a cortex or longitudinally in the direction of the haversian canals.

Example 2

Tubular Bone Allograft Model:

From this initial work a system to fully investigate the hypothesis was developed with more clinical relevance; Sections 2 cm long were cut from the diaphysial region of the sheep tibia. They were sealed at one end by cementing on an acrylic disc using cyanoacrylate glue. The open end of the tube of bone had a 3 cm long acrylic tube cemented to it, effectively extending the medullary canal and thereby increasing its volume. The specimen was then placed in a beaker to the inside of which 3 vertical equally spaced carbon electrodes were fixed. The beaker was then filled with normal saline solution to just below the open end of the acrylic tube. Two ml of the ionic compound under investigation was placed in the medullary canal of the tibia and a carbon electrode lowered into it. The effect of a potential difference applied across the cortex could thus be studied. Control specimens were prepared in an identical fashion, except no potential difference was applied across the electrodes. Study specimens had the potential difference applied for 1 minute, 2 minutes, 5 minutes or 10 minutes.

All specimens were then removed and the medullary canal washed clean and dried. Axial sections were then cut using a diamond saw and the amount of penetration of the methylene blue measured. In addition histological sections were prepared 300 $\mu$m thick to assess the penetration at a microscopic level. The methylene blue iontophoresis provided a qualitative analysis of iontophoresis in bone.

With the system set up as described, and methylene blue as the ionic solution the typical current that flowed during iontophoresis of the specimens was 40 mamp. The blue coloration of the periosteal surface was noted by approximately 1.5 minutes and by 5 minutes was maximal.

Macroscopic evaluation of the specimens subsequently was done to evaluate the penetration of the methylene blue and microscopic evaluation done to assess the uniformity of penetration. The results of this are shown in Table 1

This work was duplicated using sections of human allograft tibia. The results were found to be comparable to the sheep model. The only appreciable difference between the two was that the sheep tibiae consisted purely of compact cortical bone whereas the human tibiae comprised cortical bone on the periosteal aspect, with cancellous bone on the endosteal aspect. This cancellous bone was no barrier to diffusion of the methylene blue. The rate of facilitated diffusion and the uniformity of penetration were comparable.

TABLE 1

| Macroscopic | Microscopic |
| --- | --- |
| Control | |
| Minimal Penetration (Staining of endosteal Surface with few Volkman's canals staining for variable distance) | Staining on endosteal surface with volkman's canals filled for variable distance. No staining of bony matrix |
| 1 Minute | |
| Penetration 1.5 mm | Uniform staining of matrix to level of penetration. Filling of Volkman's canals through full thickness of cortex |
| 2 Minutes | |
| Penetration 3 mm | Uniform staining of matrix to level of penetration. Filling of Volkman's canals through full thickness of cortex |
| 5 Minutes | |
| Penetration full thickness of cortex. (Patchy staining of periosteal surface) | Complete uniform penetration of entire thickness of cortical bone matrix and Volkman's canals |

Example 3

Quantitative analysis was then carried out to test iontophoresis as a means of antibiotic delivery in allograft bone. Specimens of sheep tibia were prepared as described above. The medullary canal was filled with 2 ml of 1% gentamicin Sulphate solution (Delta West, Western Australia) or 1% flucloxacillin Sodium solution (Alphapharm) in distilled water. A potential difference of 100 volts was applied for 1 minute, 5 minutes or 10 minutes with controls being set up the same way for 10 minutes except no potential difference was applied. A recording of current passed for each specimen was made.

Each sample was then washed in water and dried. Samples from 10 the endosteal and periosteal surfaces were then taken by drilling the bone using a 3 mm low speed drill, in 10 positions on each surface, and crushed to a fine powder. To a known mass of each sample was added distilled water (2 ml) and the sample agitated using ultrasound. The sample was then centrifuged and the supernatant removed and the process repeated a further 2 times. The last wash was left to soak for 12 hours before centrifuging. The Fucloxacillin specimens were refrigerated to 4° C. during this to minimise degradation by hydrolysis. The supernatant solutions were then analysed for antibiotic content; for gentamicin using Fluorescence Polarisation Immuno Assay (Abbot Axsym Analyser); and for flucloxacillin the assays were performed using High Performance Liquid Chromatography (HPLC) technique. From the levels in the supernatant solutions, the antibiotic concentrations in the bone samples were calculated.

To study the thermal effects of iontophoresis on bone, some samples were prepared and a fibre optic thermal fluorescence probe was introduced into the centre of the cortical bone via a 0.8 mm drill hole in the long axis of the specimen. The apparatus was otherwise set up as above and then cooled to 10° C. The iontophoretic potential difference was then applied at 100 volts for 15 minutes and a continuous recording of the temperature made.

Figure 4:
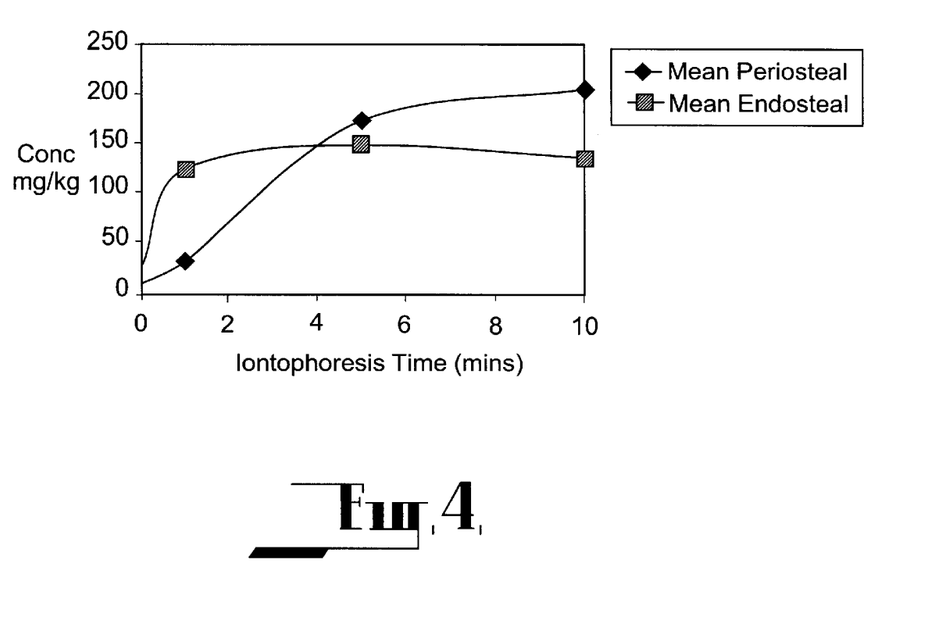
FIG. 4 illustrates a graph of gentamicin iontophoresis using sheep tibia.
Figure 5:
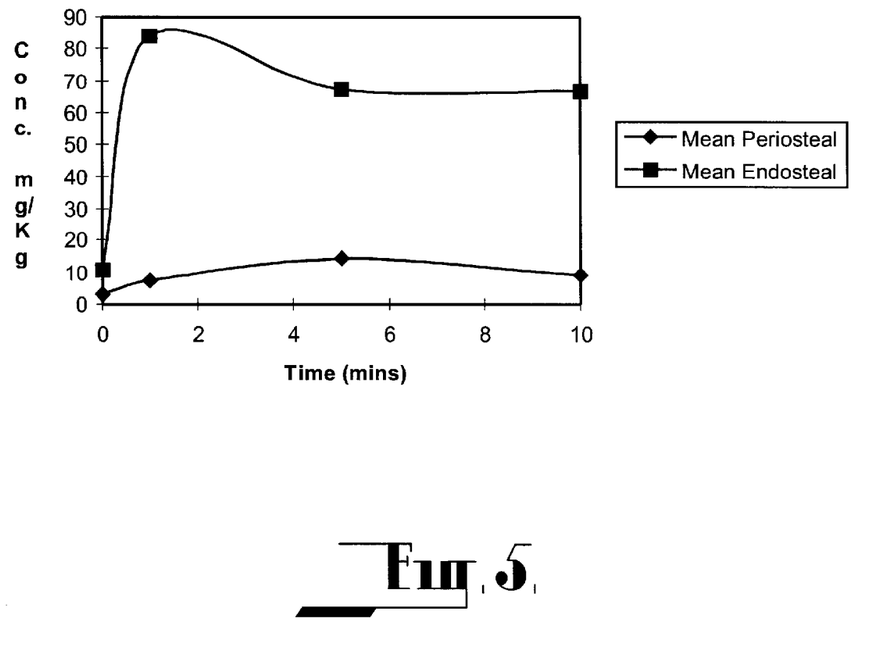
FIG. 5 illustrates a graph of flucloxacillin iontophoresis using sheep tibia.

Initial work was carried out using the sheep tibia model of allograft tubular bone. For each control and iontophoretic group, 5 specimens were used. Samples from the endosteal and periosteal surfaces were processed separately. The results are shown in FIGS. 4 & 5.

It can be seen from these graphs, that both flucloxacillin and gentamicin ions are moved through sheep cortex by the iontophoretic gradient. The levels of gentamicin achieved in both endosteal and periosteal specimens plateau at about 150 mg/Kg. This compares with recommended peak serum concentrations after intravenous administration of the drug of 10 mg/L. The minimum inhibitory concentration of gentamicin to *Staphylococcus aureus* is approximately 0.25 mg/L (although this varies with different phage types). The peak in the endosteal specimens was reached by 1 minute, and the periosteal samples at 5 minutes. This is due to the fact that the ions have further to travel to reach the periosteal surface, and consequently take longer.

Figure 6:
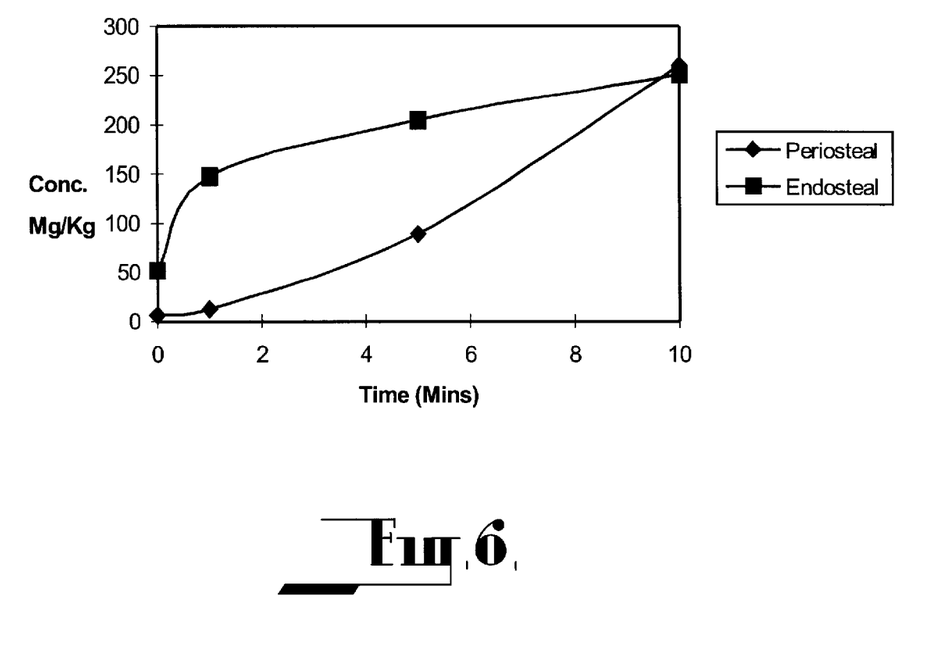
FIG. 6 illustrates a graph of gentamicin iontophoresis using human allograft.
Figure 7:
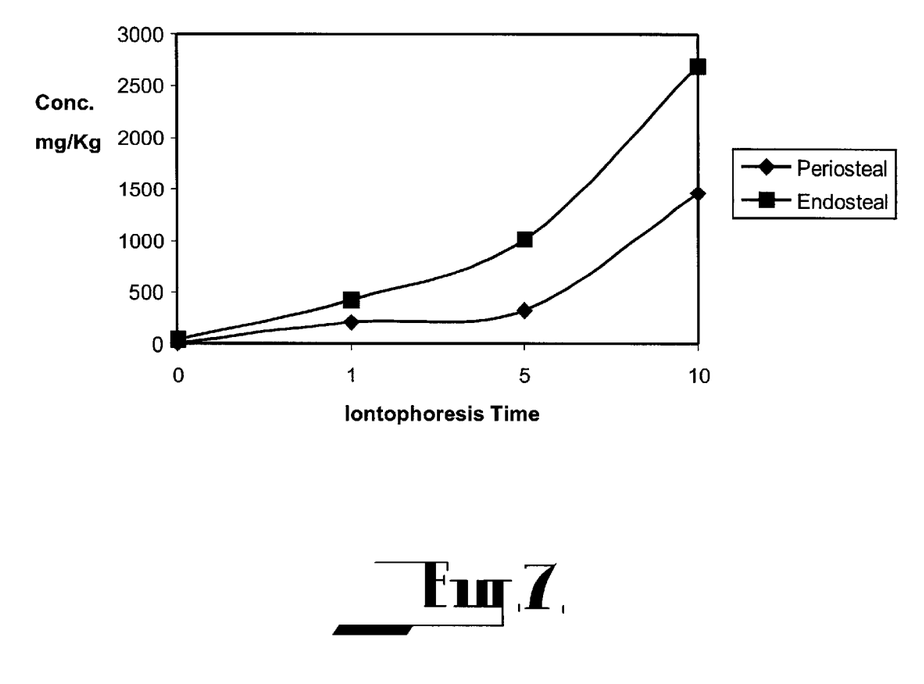
FIG. 7 illustrates a graph of flucloxacillin iontophoresis using human allograft.

This work was supplemented by repeating the study using human allograft tibia. The scarcity of available allograft bone necessitated that each group contained only one specimen. All 4 specimens were contiguous 1 cm sections of the diaphysis of the same non-irradiated tibia for each of gentamicin and flucloxacillin. The results are shown in FIGS. 6 & 7.

Gentamicin and flucloxacillin behave in a similar fashion in human allograft bone to sheep bone. Again therapeutic levels of antibiotic are achieved although the time to reach maximal levels at all depths was 10 minutes. This increase in time probably reflects the increase thickness of the human specimens compared with the sheep specimens.

Figure 8:
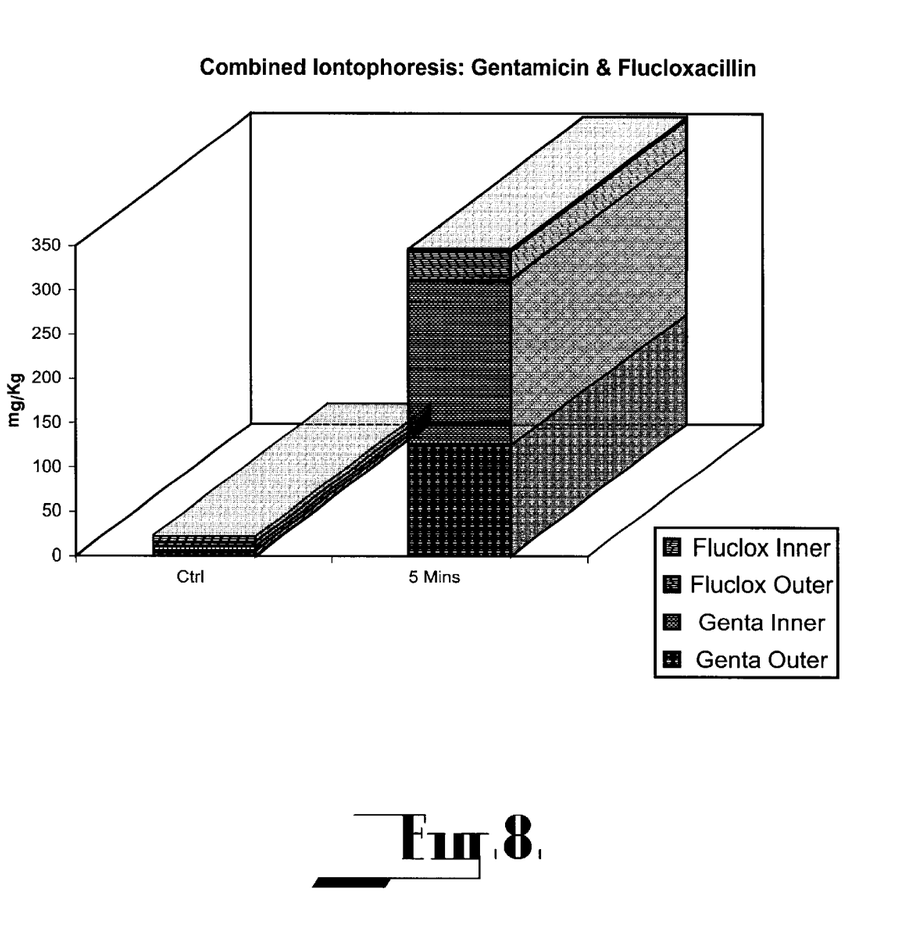
FIG. 8 illustrates a graph of the combined iontophoresis using gentamicin and flucloxacillin.

As gentamicin migrates from the anode and flucloxacillin migrates from the cathode, the next step to investigate was the possibility of simultaneous iontophoresis of each drug in opposite directions across sheep tibia specimens. The set up was as previously used, the gentamicin 1% solution being placed in the medullary canal with the anode and the flucloxacillin 1% solution being placed in the beaker, thus bathing the cathode. The results of this are shown in FIG. 8.

As can be seen here, gentamicin penetrates the full thickness of the cortex after 5 minutes of iontophoresis, whereas the flucloxacillin levels in the periosteal samples only are elevated. The total antibiotic concentration is markedly elevated when compared with the controls.

Example 4

The bioavailability of the antibiotics was assessed by creating specimens using the above iontophoretic technique and applying the potential difference for 5 minutes. Samples were then drilled from the cortices and prepared as above for assay of the starting antibiotic concentration. Each specimen was then immersed in 20 mls of Normal Saline. This solution was poured off at intervals and antibiotic levels assayed in the solution. Each sample was immediately re immersed in fresh solution. In this way the rate of elution of the iontophoresed antibiotic could be studied. Again, the gentamicin samples were kept at ambient temperature the flucloxacillin samples being refrigerated to 4° C. The final elution assay was carried out at 14 days. The bioactivity of the antibiotics loaded into bone by iontophoresis was investigated. Specimens of sheep tibia were prepared: ⅓ having had no exposure to antibiotics, ⅓ having been soaked for 5 minutes in antibiotic solution and ⅓ having been loaded with antibiotic using iontophoresis as per the above technique for 5 minutes with a potential difference of 100 volts. From each specimen a 1 mm thick axial section was cut using a diamond saw and this was placed on a nutrient agar plate with a standard *Staphylococcus aureus* preparation (fully sensitive). The plates were then incubated for 24 hours and the zone of inhibition inspected and measured.

Figure 9:
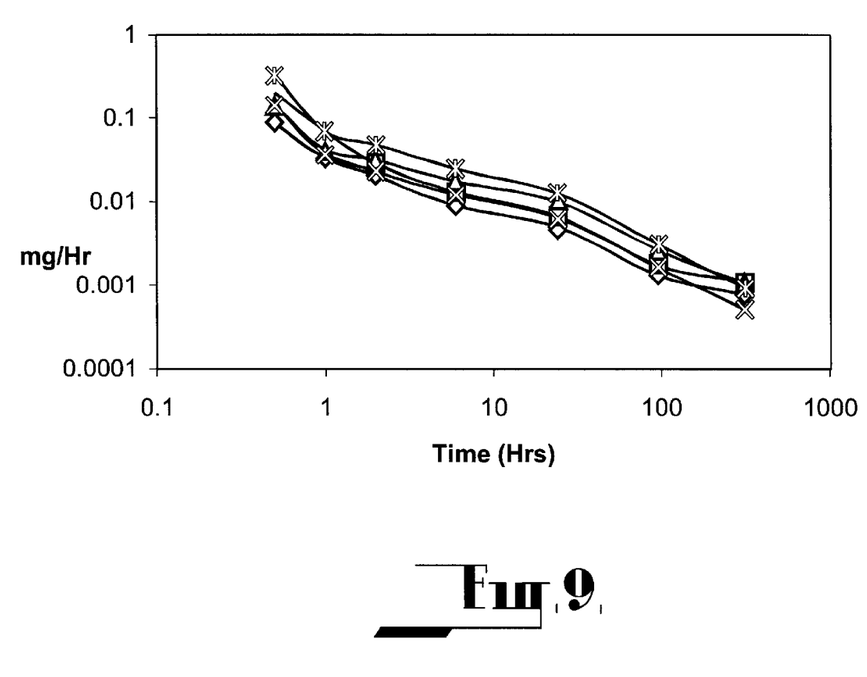
FIG. 9 illustrates a graph of hourly gentamicin washout per mg antibiotic available.
Figure 10:
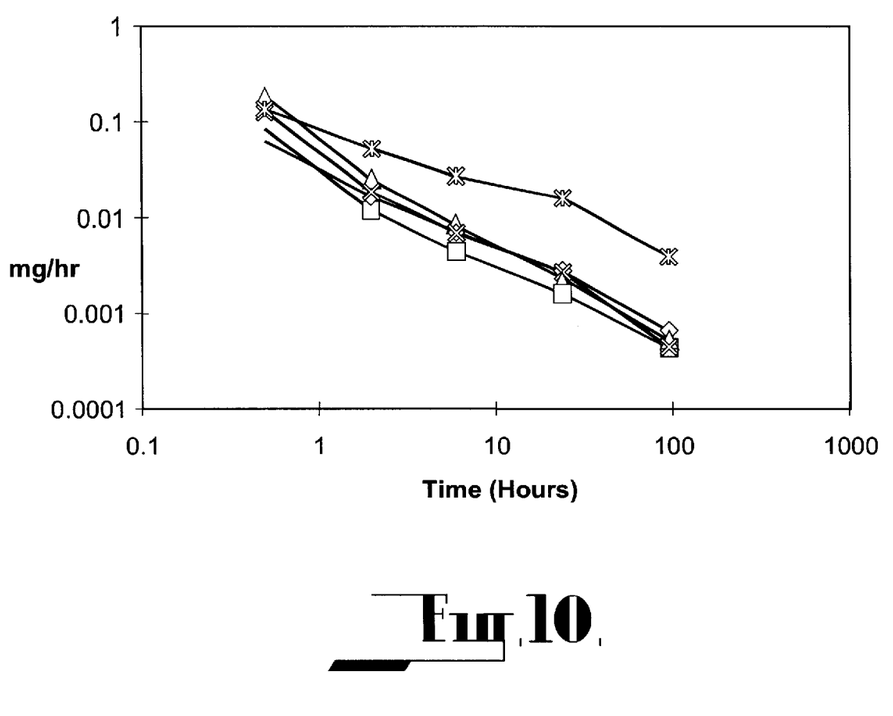
FIG. 10 illustrates a graph of hourly flucloxacillin washout per mg antibiotic available.

The results for the rates of dissolution of the antibiotics from tubular sections of bone 2 cm long, (approx. 5 g weight) in 20 ml of saline are shown in FIGS. 9 & 10.

Both antibiotics behaved in a similar fashion, with a logarithmic decrease in their rates of dissolution. There was still antibiotic becoming available up to two weeks after soaking the bone in normal saline solution.

Figure 11A:
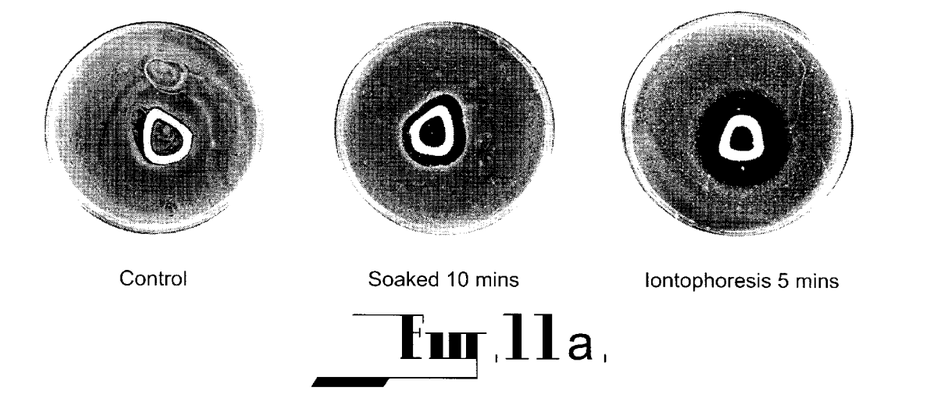
FIG. 11(a) illustrates gentamicin bioactivity against *Staphylococcus Aureus*.
Figure 11B:
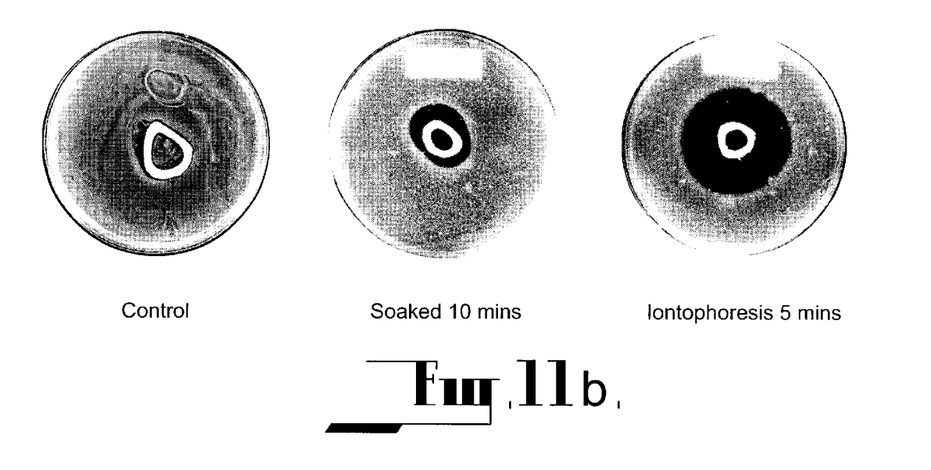
FIG. 11(b) illustrates flucloxacillin bioactivity against *Staphlococcus Aureus*.

Bioactivity of Antibiotics after Iontophoresis: The results of the nutrient agar plate test of the drugs activity against a fully sensitive Staphylococcus are shown in FIGS. 11*a* and 11*b*.

While bacterial colonies can be seen growing up to the bone in the case of bone which has never been exposed to antibiotic there is a zone of inhibition of growth around the bone for those soaked in antibiotic and a larger zone of inhibition around the iontophoresis specimens.

Figure 12:
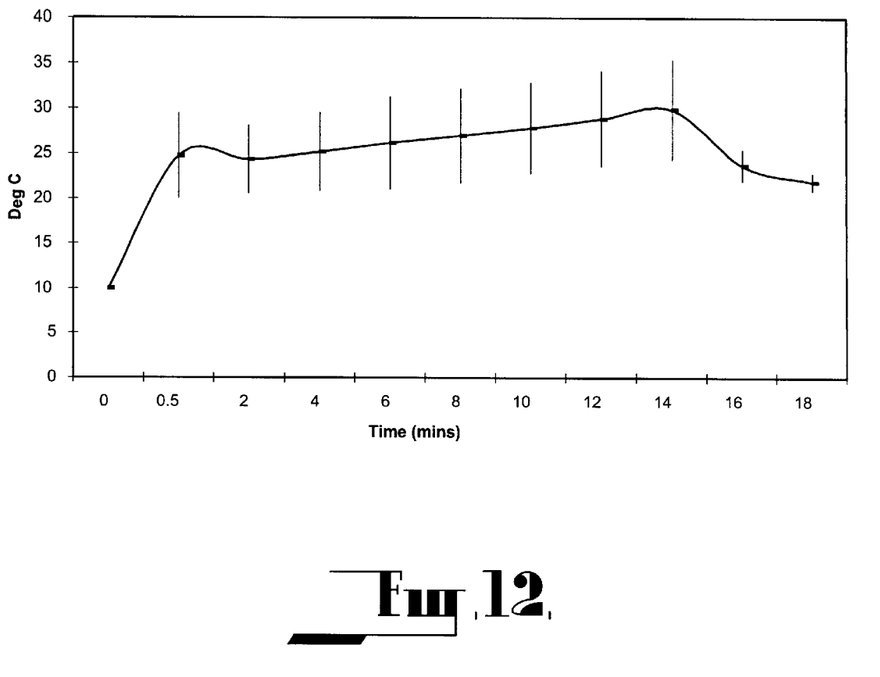
FIG. 12 illustrates a graph of a temperature plot.

Thermal Effects of Iontophoresis: The temperature plot is shown in FIG. 12 for the mean values of 3 specimens. All specimens were initially cooled to 10° C. The plot shows the mean values with the highest and lowest values superimposed. The iontophoretic current was turned off at 15 minutes and recordings of temperature made for a further 3 minutes.

After an initial rapid rise in the first 30 seconds the temperature increases slowly until the current is turned off at 15 minutes. The highest temperature recorded was 35.7° C. This thermal effect is result of the energy dissipation of the 40 mamp current being passed at 100 volts potential difference representing a power generation of 4 watts energy, within the system as a whole.

The results of this work demonstrate that high concentrations of both gentamicin and flucloxacillin can be achieved in sheep tibia after 1 minute and human allograft tibia after 5 minutes of iontophoresis. The procedure is simple and requires no expensive equipment. Further allograft bone may be treated in this way at the time of defrosting the graft prior to implantation in the operating room.

An attempt to simultaneously move gentamicin and flucloxacillin in opposite directions across a cortex has shown that gentamicin moves full thickness, but flucloxacillin penetrates only the periosteal side. This is most likely due to the precipitation reaction encountered when solutions of gentamicin and flucloxacillin are mixed. The implication in clinical practice is that the gentamicin will penetrate well using this system, but the periosteal surface of the bone will in addition achieve therapeutic levels of flucloxacillin. The preliminary work with methylene blue has shown that this is likely to be the surface that receives the least predictable amount of positively charged ion (in this case, gentamicin.).

While the levels of gentamicin in the bone may appear alarmingly high, if a 500 g allograft containing 200 mg/Kg were to be implanted, the total dose of drug being implanted is about 100 mg, which is well below the usual daily dose of gentamicin on a once daily intravenous regime. The method of calculation of antibiotic concentration in bone has assumed that all antibiotic is washed out of the crushed bone. The levels of antibiotic described above are also considerably higher than levels that have been measured in bone after intravenous administration which vary from 2.4–19.4 mg/Kg and usually reach levels between 0.14 and 0.36 of serum concentration.

It should be understood that the foregoing description of the invention including the principles, preferred embodiments and Examples cited above are illustrative of the invention and should not be regarded as being restrictive on its scope. Variations and modifications may be made to the invention by others without departing from the spirit of that which is described as the invention and it is expressly intended that all such variations and changes which fall within this ambit are embraced thereby is intended merely to be illustrative thereof.

The claims defining the invention are as follows:

1. A method for supplementing bone or bone tissue with a therapeutically useful compound, comprising the steps of:
   (a) exposing bone or bone tissue in vitro or ex vivo to a therapeutically useful compound; and
   (b) applying a potential difference across said bone or bone tissue such that the therapeutically useful compound is concentrated within the bone or bone tissue.

2. The method according to claim 1, wherein the therapeutically useful compound is concentrated within the bone or bone tissue by an externally applied potential difference.

3. The method according to claim 1, wherein the therapeutically useful compound is selected from the group consisting of antibiotics, antifungal compounds, chemotherapeutic compounds, tissue growth factors, non-steroidal anti-inflammatory agents, such as indomethacin, neuromuscular agents affecting calcium and bone metabolism, antiviral agents, anti-tuberculosis agents, anthelmintic agents, antiseptic agents, vitamins and minerals.

4. The method according to claim 1, wherein the therapeutically useful compound forms a salt in solution and ionises to a single positive or negative ion.

5. The method according to claim 4, wherein the therapeutically useful compound is an antibiotic selected from the group consisting of flucloxacillin, gentamycin, cephalothin, ticarcillin, ciprofloxacin, nenzl-penicillin, cefoperazone, cefuroxime, cephazolin and tobramycin.

6. The method according to claim 5, wherein the antibiotic is gentamycin and wherein it is loaded into the bone or bone tissue at a maximum dose of about 200 mg/kg.

7. The method according to claim 5, wherein the antibiotic is flucloxacillin and wherein it is loaded into the bone or bone tissue at a maximum dose of about 80 mg/kg.

8. The method according to claim 4, wherein the therapeutically useful compound is an antifungal compound selected from the group consisting of miconazole and ketaconazole.

9. The method according to claim 4, wherein the therapeutically useful compound is a chemotherapeutic compound selected from the group consisting of 5-fluoro-uracil and vinblastin.

10. A bone or bone tissue supplemented with at least a therapeutically useful compound, wherein said compound is concentrated within the bone or bone tissue according to the method defined by claim 1.

11. The bone or bone tissue according to claim 10, wherein the therapeutically useful compound is concentrated to an amount between the minimum concentration required for activity of the compound in vivo and the maximum concentration that is equal to the safe maximum single dose for systemic administration.

12. The bone or bone tissue according to claim 10 or 11, wherein the therapeutically useful compound is selected from the group consisting of antibiotics, antifungal compounds, chemotherapeutic compounds, tissue growth factors, non-steroidal anti-inflammatory agents, such as indomethacin, neuromuscular agents affecting calcium and bone metabolism, anti-viral agents, anti-tuberculosis agents, anthelmintic agents, antiseptic agents, vitamins and minerals.

13. The bone or bone tissue according to claim 10 or 11, wherein the therapeutically useful compound forms a salt in solution and ionises to a single positive or negative ion.

14. The bone or bone tissue according to claim 13, wherein the therapeutically useful compound is an antibiotic selected from the group consisting of flucloxacillin, gentamycin, cephalothin, ticarcillin, ciprofloxacin, nenzlpenicillin, cefoperazone, cefuroxime, cephazolin and tobramycin.

15. The bone or bone tissue according to claim 14, wherein the antibiotic is gentamycin and wherein it is loaded into the bone or bone tissue at a maximum dose of about 200 mg/kg.

16. The bone or bone tissue according to claim 14, wherein the antibiotic is flucloxacillin and wherein it is loaded into the bone or bone tissue at a maximum dose of about 80 mg/kg.

17. The bone or bone tissue according to claim 14, wherein the therapeutically useful compound is an antifungal compound selected from the group consisting of miconazole and ketaconazole.

18. The bone or bone tissue according to claim 14, wherein the therapeutically useful compound is a chemotherapeutic compound selected from the group consisting of 5-fluoro-uracil and vinblastine.

* * * * *